United States Patent
Kozloski et al.

(10) Patent No.: US 10,653,353 B2
(45) Date of Patent: *May 19, 2020

(54) MONITORING A PERSON FOR INDICATIONS OF A BRAIN INJURY

(71) Applicant: INTERNATIONAL BUSINESS MACHINES CORPORATION, Armonk, NY (US)

(72) Inventors: James R. Kozloski, New Fairfield, CT (US); Mark C. H. Lamorey, Williston, VT (US); Clifford A. Pickover, Yorktown Heights, NY (US); John J. Rice, Mohegan Lake, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 31 days.

This patent is subject to a terminal disclaimer.

(21) Appl. No.: 14/744,064

(22) Filed: Jun. 19, 2015

(65) Prior Publication Data
US 2016/0278686 A1    Sep. 29, 2016

Related U.S. Application Data

(63) Continuation of application No. 14/664,991, filed on Mar. 23, 2015.

(51) Int. Cl.
*A61B 5/00*           (2006.01)
*A61B 5/11*           (2006.01)
(Continued)

(52) U.S. Cl.
CPC ............ *A61B 5/4064* (2013.01); *A61B 3/112* (2013.01); *A61B 3/113* (2013.01); *A61B 5/112* (2013.01);
(Continued)

(58) Field of Classification Search
CPC ..... A61B 5/112; A61B 5/6804; A61B 5/1116; A61B 5/6803; A61B 5/7271; A61B 5/4064; A61B 5/746
See application file for complete search history.

(56) References Cited

U.S. PATENT DOCUMENTS

| 4,172,495 A | 10/1979 | Zebuhr et al. |
| 5,261,399 A | 11/1993 | Klatz et al. |

(Continued)

FOREIGN PATENT DOCUMENTS

| CA | 2772644 A1 | 1/2013 |
| WO | 2014062738 A1 | 4/2014 |
| WO | 2014076698 A1 | 5/2014 |

OTHER PUBLICATIONS

Parker, et al. "Gait stability following concussion." Medicine & Science in Sports & Exercise 38.6 (2006): 1032-1040.*

(Continued)

*Primary Examiner* — David J. McCrosky
(74) *Attorney, Agent, or Firm* — Cantor Colburn LLP; Vazken Alexanian

(57) ABSTRACT

Embodiments include methods, systems and computer program products for monitoring a person for a traumatic brain injury. Aspects include monitoring a gait of the user with one or more accelerometers embedded in the uniform and analyzing, by a processor, one or more characteristics of the gait of the user. Aspects also include determining whether the one or more characteristics of the gait indicate that the user may have suffered the traumatic brain injury and creating an alert that the user of the helmet may have suffered the traumatic brain injury.

3 Claims, 9 Drawing Sheets

(51) Int. Cl.
  *A61B 3/113* (2006.01)
  *A61B 3/11* (2006.01)
(52) U.S. Cl.
  CPC ........... *A61B 5/6803* (2013.01); *A61B 5/1116* (2013.01); *A61B 5/746* (2013.01); *A61B 2560/0242* (2013.01); *A61B 2562/0204* (2013.01); *A61B 2562/0219* (2013.01)

(56) References Cited

U.S. PATENT DOCUMENTS

| | | | |
|---|---|---|---|
| 5,708,988 | A | 1/1998 | McGuine et al. |
| 6,007,086 | A | 12/1999 | Hopkins |
| 6,065,158 | A | 5/2000 | Rush, III |
| 6,081,929 | A | 7/2000 | Rothrock et al. |
| 6,090,051 | A | 7/2000 | Marshall |
| 6,163,250 | A | 12/2000 | Moskowitz |
| 6,198,394 | B1 | 3/2001 | Jacobsen et al. |
| 6,240,571 | B1 | 6/2001 | Infusino |
| 6,277,143 | B1 | 8/2001 | Klatz et al. |
| 6,665,884 | B1 | 12/2003 | Demps et al. |
| 6,826,509 | B2 | 11/2004 | Crisco, III et al. |
| 6,941,952 | B1 | 9/2005 | Rush, III |
| 7,016,730 | B2 * | 3/2006 | Ternes ............... A61N 1/3708 607/14 |
| 7,294,107 | B2 | 11/2007 | Simon |
| 7,396,654 | B2 | 7/2008 | Hayes et al. |
| 7,433,520 | B1 | 10/2008 | David |
| 7,526,389 | B2 | 4/2009 | Greenwald et al. |
| 7,665,845 | B2 | 2/2010 | Kiderman et al. |
| 8,087,254 | B2 | 1/2012 | Arnold |
| 8,126,731 | B2 | 2/2012 | Dicks et al. |
| 8,466,794 | B2 | 6/2013 | Mack et al. |
| 8,499,365 | B1 | 8/2013 | Hill |
| 8,548,768 | B2 * | 10/2013 | Greenwald .......... A61B 5/6803 600/595 |
| 8,585,609 | B2 | 11/2013 | Kiderman et al. |
| 8,603,151 | B2 | 12/2013 | Latham |
| 8,621,673 | B1 | 1/2014 | Pietrantonio |
| 8,678,897 | B2 | 3/2014 | Englert et al. |
| 9,226,707 | B2 | 1/2016 | Huang |
| 9,351,141 | B2 | 5/2016 | Jacobsen |
| 9,576,593 | B2 | 2/2017 | Pakhomov et al. |
| 9,642,571 | B2 | 5/2017 | McIntosh et al. |
| 9,642,574 | B2 | 5/2017 | Zhavoronkov et al. |
| 2002/0183657 | A1 | 12/2002 | Socci et al. |
| 2003/0097845 | A1 | 5/2003 | Saunders et al. |
| 2004/0064171 | A1 | 4/2004 | Briscoe et al. |
| 2004/0220498 | A1 | 11/2004 | Li et al. |
| 2004/0225199 | A1 | 11/2004 | Evanyk et al. |
| 2005/0067816 | A1 | 3/2005 | Buckman |
| 2005/0177929 | A1 | 8/2005 | Greenwald et al. |
| 2005/0273017 | A1 | 12/2005 | Gordon |
| 2006/0189652 | A1 | 8/2006 | Lampilas et al. |
| 2006/0189852 | A1 | 8/2006 | Greenwald et al. |
| 2006/0191049 | A1 | 8/2006 | Elkins et al. |
| 2006/0224048 | A1 | 10/2006 | Devaul et al. |
| 2007/0050715 | A1 | 3/2007 | Behar |
| 2007/0084496 | A1 | 4/2007 | Edey |
| 2007/0137685 | A1 | 6/2007 | Jwo et al. |
| 2008/0158502 | A1 | 7/2008 | Becker et al. |
| 2008/0234788 | A1 | 9/2008 | Wasowski |
| 2008/0269579 | A1 | 10/2008 | Schiebler |
| 2008/0281550 | A1 | 11/2008 | Hogle et al. |
| 2009/0221884 | A1 | 9/2009 | Ryan |
| 2010/0101005 | A1 | 4/2010 | Cripton et al. |
| 2010/0140241 | A1 | 6/2010 | Martin et al. |
| 2010/0280372 | A1 | 11/2010 | Poolman et al. |
| 2010/0292545 | A1 | 11/2010 | Berka et al. |
| 2010/0292601 | A1 | 11/2010 | Dompeling et al. |
| 2010/0319110 | A1 | 12/2010 | Preston-Powers |
| 2011/0144539 | A1 | 6/2011 | Ouchi |
| 2011/0181418 | A1 | 7/2011 | Mack et al. |
| 2011/0181419 | A1 | 7/2011 | Mack et al. |
| 2011/0181420 | A1 | 7/2011 | Mack et al. |
| 2011/0184319 | A1 | 7/2011 | Mack et al. |
| 2011/0197613 | A1 | 8/2011 | Pryor |
| 2011/0215931 | A1 | 9/2011 | Callsen et al. |
| 2011/0246123 | A1 | 10/2011 | Dellostritto et al. |
| 2012/0088222 | A1 | 4/2012 | Considine et al. |
| 2012/0124720 | A1 | 5/2012 | Evans et al. |
| 2012/0150545 | A1 | 6/2012 | Simon |
| 2012/0172677 | A1 | 7/2012 | Logan et al. |
| 2012/0188083 | A1 * | 7/2012 | Miller, II ............... A42B 3/046 340/573.1 |
| 2012/0210498 | A1 | 8/2012 | Mack |
| 2012/0214143 | A1 | 8/2012 | Severson et al. |
| 2012/0221251 | A1 | 8/2012 | Rosenberg et al. |
| 2012/0238831 | A1 | 9/2012 | Benford |
| 2012/0244555 | A1 | 9/2012 | Blyth et al. |
| 2012/0292488 | A1 | 11/2012 | Saadat |
| 2012/0297525 | A1 | 11/2012 | Bain |
| 2012/0304367 | A1 | 12/2012 | Howard et al. |
| 2013/0035613 | A1 | 2/2013 | Curtiss |
| 2013/0060168 | A1 | 3/2013 | Chu et al. |
| 2013/0060489 | A1 | 3/2013 | Crossman et al. |
| 2013/0066236 | A1 | 3/2013 | Herman et al. |
| 2013/0066448 | A1 | 3/2013 | Alonso |
| 2013/0074248 | A1 | 3/2013 | Evans et al. |
| 2013/0110415 | A1 | 5/2013 | Davis et al. |
| 2013/0127980 | A1 | 5/2013 | Haddick et al. |
| 2013/0142363 | A1 | 6/2013 | Amento et al. |
| 2013/0150684 | A1 | 6/2013 | Cooner |
| 2013/0185837 | A1 | 7/2013 | Phipps et al. |
| 2013/0211484 | A1 | 8/2013 | Rozental |
| 2013/0218053 | A1 | 8/2013 | Kaiser et al. |
| 2013/0253286 | A1 | 9/2013 | Fridmn |
| 2013/0271602 | A1 | 10/2013 | Bentley et al. |
| 2013/0312163 | A1 | 11/2013 | Van Waes |
| 2013/0314508 | A1 | 11/2013 | Arima |
| 2013/0340147 | A1 | 12/2013 | Giles |
| 2014/0020158 | A1 | 1/2014 | Parsons et al. |
| 2014/0024971 | A1 * | 1/2014 | Bunn ....................... A61B 5/11 600/595 |
| 2014/0039274 | A1 | 2/2014 | Sarrafzadeh et al. |
| 2014/0039354 | A1 | 2/2014 | Greenwald et al. |
| 2014/0073993 | A1 | 3/2014 | Poellabauer et al. |
| 2014/0121559 | A1 | 5/2014 | Stevens et al. |
| 2014/0130239 | A1 | 5/2014 | Preston-Powers |
| 2014/0142439 | A1 | 5/2014 | French |
| 2014/0159922 | A1 | 6/2014 | Maliszewski et al. |
| 2014/0173812 | A1 | 6/2014 | Krueger |
| 2014/0275807 | A1 | 9/2014 | Redei |
| 2014/0285768 | A1 | 9/2014 | Barnard et al. |
| 2014/0333446 | A1 | 11/2014 | Newlove |
| 2014/0379058 | A1 | 12/2014 | Farrago et al. |
| 2014/0379369 | A1 | 12/2014 | Kokvidis et al. |
| 2015/0037771 | A1 | 2/2015 | Kaleal, III et al. |
| 2015/0038874 | A1 | 2/2015 | Abreu |
| 2015/0094914 | A1 | 4/2015 | Abreu |
| 2015/0245795 | A1 * | 9/2015 | Rennaker ............. A61B 5/4064 600/301 |
| 2015/0375083 | A1 | 12/2015 | Stelfox et al. |
| 2016/0007910 | A1 * | 1/2016 | Boss .................. A61B 5/02055 600/301 |
| 2016/0018278 | A1 * | 1/2016 | Jeter, II .................. G01L 5/0052 340/665 |
| 2016/0125653 | A1 | 5/2016 | Denis |
| 2016/0178643 | A1 | 6/2016 | Everett et al. |
| 2016/0189852 | A1 | 6/2016 | Jeon et al. |
| 2016/0310819 | A1 | 10/2016 | Allen et al. |
| 2016/0369861 | A1 | 12/2016 | Phipps et al. |

OTHER PUBLICATIONS

Kozloski et al. U.S. Appl. No. 14/664,991, filed Mar. 23, 2015; Entitled: Monitoring a Person for Indications of a Brain Injury.
Kozloski et al., U.S. Appl. No. 14/664,987, filed Mar. 23, 2015; Entitled: Monitoring a Person for Indications of a Brain Injury.
Kozloski et al., U.S. Appl. No. 14/664,989, filed Mar. 23, 2015; Entitled: Monitoring a Person for Indications of a Brain Injury.
Kozloski et al., U.S. Appl. No. 14/709,563, filed May 12, 2015; Entitled: "Helmet Having a Cumulative Concussion Indicator".

(56) References Cited

OTHER PUBLICATIONS

Kozloski et al., U.S. Appl. No. 14/709,564, filed May 12, 2015; Entitled: "Monitoring Impacts Between Individuals for Concussion Analysis".
Kozloski et al., U.S. Appl. No. 14/709,568, filed May 12, 2015; Entitled: "Helmet Having an Embedded Cooling Array".
Kozloski et al., U.S. Appl. No. 14/709,570, filed May 12, 2015; Entitled: "Mouthguard for Analysis of Biomarkers for Traumatic Brain Injury".
Kozloski et al., U.S. Appl. No. 14/709,572, dated May 12, 2015; Entitled: "Suggesting Adjustments to a Helmet Based on Analysis of Play".
Kozloski et al., U.S. Appl. No 14/709,574, filed May 12, 2015; Entitled: "Automatic Adjustment of Helmet Parameters Based on a Category of Play".
Kozloski et al., U.S. Appl. No. 14/709,575, filed May 12, 2015; Entitled: "Detection of a Traumatic Brain Injury with a Mobile Device".
Kozloski et al., U.S. Appl. No. 14/744,061, filed Jun. 19, 2015; Entitled: Monitoring a Person for Indications of a Brain Injury.
Kozloski et al., U.S. Appl. No. 14/744,063, filed Jun. 19, 2015; Entitled: Monitoring a Person for Indications of a Brain Injury.
Kozloski et al., U.S. Appl. No. 14/745,491, filed Jun. 22, 2015; Entitled: "Automatic Adjustment of Helmet Parameters Based on a Category of Play".
Kozloski et al., U.S. Appl. No. 14/745,492, filed Jun. 22, 2015; Entitled: "Detection of a Traumatic Brain Injury with a Mobile Device".
Kozloski et al., U.S. Appl. No. 14/745,493, filed Jun. 22, 2015; Entitled: "Suggesting Adjustments to a Helmet Based on Analysis of Play".
Kozloski et al., U.S. Appl. No. 14/745,494, filed Jun. 22, 2015; Entitled: "Mouthguard for Analysis of Biomarkers for Traumatic Brain Injury".
Kozloski et al., U.S. Appl. No. 14/745,495, filed Jun. 22, 2015; Entitled: "Helmel Having an Embedded Cooling Array".
Kozloski et al., U.S. Appl. No. 14/745,497, filed Jun. 22, 2015; Entitled: "Monitoring Impacts Between Individuals for Concussion Analysis".
Kozloski et al., U.S. Appl. No. 14/745,498, filed Jun. 22, 2015; Entitled: "Having a Cumulative Concussion Indicator".
Zimmerman, T.G. "Personal Area Networks: Near-field intrabody communication", IBM Systems Journal, vol. 35, Nos. 3 and 4, 1996; pp. 609-617.
Adoni et al., "The pupillary response in traumatic brain injury: A guide for trauma nurses," Journal of Trauma Nursing, vol. 14, No. 4, 2007, pp. 191-196.
Caswell et al., "Development of Nanoparticle-Enabled Protein Biomarker Discovery: Implementation for Saliva-Based Traumatic Brain Injury Detection", Advances in Salivary Diagnostics, Springer-Verlag Berlin Heidelberg 2015, pp. 121-129.
Chen, Jeff W. et al. "Pupillary reactivity as an early indicator of increased intracranial pressure: The introduction of the Neurological Pupil Index" Surg. Neurol. Int. 2011; 2:82; published online Jun. 21, 2011; URL: https://www.ncbi.nlm.nih.gov/pmc/articles/PMC3130361/ ; 13 pgs.
Chow et al., "Intersegmental coordination of gait after hemorrhagic stroke," Experimental Brain Research, Published Online, Sep. 17, 2014, 11 pages. http://rd.springer.com/article/10.1007/s00221-014-4099-2.
Eye News "A practical guide to anisocoria", Feb./Mar. 2018, vol. 24, No. 5; www.eyenews.uk.com; 2 pgs.
Funk et al., "Validation of Concussion Risk Curves for Collegiate Football Players Derived from HITS Data", Annals of Biomedical Engineering, vol. 40, No. 1, Jan. 2012; pp. 79-89.
Ghajar, "Traumatic brain injury," The Lancet, vol. 356, No. 9233, 2000, pp. 923-929.Ghajar, "Traumatic brain injury," The Lancet, vol. 356, No. 9233, 2000, pp. 923-929.
Guskiewicz et al., "Chapter 3 The Biomechanics and Pathomechanics of Sport-Related Concussion Looking at History to Build the Future", Springer US, 2006, pp. 65-83.
Gwin et al., "An Investigation of the NOCSAE Linear Impactor Test Method Based on In Vivo Measures of Head Impact Acceleration in American Football", Journal of Biomechanial Engineering, vol. 132, No. 1, 2010, 011006, 9 pgs.
Harris et al., "Forced Convective head cooling device reduces human cross-sectional brain temperature measured by magnetic resonance: a non-randomized healthy volunteer pilot study", British Journal of Anaesthesia, vol. 100, No. 3, 2008; pp. 365-372.
Jaeger et al., "Speech Disorders following Severe Traumatic Brain Injury: Kinamatic Analysis of Syllable Repetitions Using Electromagnetic Articulography", Folia Phoniatrica ET Logopaedica, vol. 52, No. 4, 2000, pp. 187-196.
Lathan et al., "Defense Automated Neurobehavioral Assessment (DANA)—Psychometric Properties of a New Field-Deployable Neurocognitive Assessment Tool" Military Medicine, vol. 178, 4:365, Apr. 2013; pp. 365-371.
Li et al., "Feature extraction from ear-worn sensor data for gait analysis," IEEE-EMBS International Conference on Biomedical and Health Informatics (BHI), 2014, pp. 560-563.
Muro-De-La-Herran et al., "Gait Analysis Methods: An Overview of Wearable and Non-Wearable Systems, Highlighting Clinical Applications", Sensors 2014, 14, 3362-3394.
Rowson et al., "Development of the STAR Evaluation System for Football Helmets: Integrating Player Head Impact Exposure and Risk of Concussion", Annals of Biomedical Engineering, vol. 39, No. 8, Aug. 2011; pp. 2130-2140.
Russo et al., "Test-retest reliability of the Defense Automated Neurobehavioral Assessment (DANA) tool as administered to a homogeneous population of healthy Collegiate Athletes", Preprint submitted to Journal of Mathematical psychology Jan. 25, 2014; 15 pgs.
Sahler et al., "Traumatic Brain Injury in Sports: A Review", Rehabilitation Research and Practice, vol. 2012, 2012, 659652, 10 pgs.
Samuel, C. et al., "Dysprosody after severe closed head injury: an acoustic analysis"; Journal of Neurology, Neurosurgery & Psychiatry; vol. 64, No. 4, 1998: pp. 482-485.
Saxena et al., "Direct brain cooling versus systemic hypothermia following acute brain injury", IHE, Feb. Mar. 2006, 2 pgs.
Toshniwal et al., "Residual speech impairment in patients with traumatic brain injury", the Indian Journal of Neurotrauma, vol. 7, No. 1, 2010, pp. 61-66.
Wang et al., "A Novel Head-Neck Cooling Device for Concussion Injury in Contact Sports", Translational Neuroscience, vol. 6, No. 1, 2015, pp. 20-31.
Wilcox et al., "Head-Impact Mechanisms in Men's and Women's Collegiate Ice Hocky", Journal of Athletic Training, 2014, vol. 49, No. 4, Aug. 2014, pp. 514-520.

\* cited by examiner

MONITORING A PERSON FOR INDICATIONS OF A BRAIN INJURY

DOMESTIC PRIORITY

This application is a continuation of U.S. application Ser. No. 14/664,991; Filed: Mar. 23, 2015; which is related to U.S. application Ser. No. 14/664,987; Filed Mar. 23, 2015; and U.S. application Ser. No. 14/664,989; Filed Mar. 23, 2015; the contents of each of which are herein incorporated by reference in their entirety.

BACKGROUND

The present disclosure relates to monitoring a person for indications of a brain injury, and more specifically, to methods, systems and computer program products for using sensors in a uniform to monitor a person for indications of a brain injury.

Generally speaking, safety is a primary concern for both users of helmets and manufacturers of helmets. Helmets are used by individuals that participate in activities that have risk of head trauma, such as the area of sports, biking, motorcycling, etc. While helmets have traditionally been used to provide protection from blunt force trauma to the head, an increased awareness of concussion causing forces has motivated a need for advances in helmet technology to provide increased protection against concussions. A concussion is a type of traumatic brain injury that is caused by a blow to the head that shakes the brain inside the skull due to linear or rotational accelerations. Recently, research has linked concussions to a range of health problems, from depression to Alzheimer's, along with a range of brain injuries. Unlike severe traumatic brain injuries, which result in lesions or bleeding inside the brain and are detectable using standard medical imaging, a concussion is often invisible in brain tissue, and therefore only detectable by means of a cognitive change, where that change is measurable by changes to brain tissue actions, either neurophysiological or through muscle actions caused by the brain and the muscles resulting effects on the environment, for example, speech sounds.

Currently available helmets use accelerometers to measure the forces that the helmet, and therefore the head of the user, experiences. These accelerometers can be used to indicate when a force experienced by a helmet may be sufficiently large so as to pose a risk of a concussion to the user. However, currently available helmets are prone to providing false positives which can lead to unnecessary downtime for the user of the helmet. In addition, a large number of false positives may lead to individuals disregarding the indications generated and therefore a further degradation of the effectiveness of the monitoring.

SUMMARY

In accordance with an embodiment, a method for monitoring a user of a helmet for a traumatic brain injury includes monitoring a gait of the user with one or more accelerometers embedded in the uniform and analyzing, by a processor, one or more characteristics of the gait of the user. The method also includes determining whether the one or more characteristics of the gait indicate that the user may have suffered the traumatic brain injury and creating an alert that the user of the helmet may have suffered the traumatic brain injury.

In accordance with another embodiment, a uniform for monitoring a user of for a traumatic brain injury includes a processor and one or more accelerometers. The processor is configured to perform a method that includes monitoring a gait of the user with one or more accelerometers embedded in the uniform and analyzing one or more characteristics of the gait of the user. The method also includes determining whether the one or more characteristics of the gait indicate that the user may have suffered the traumatic brain injury and creating an alert that the user of the helmet may have suffered the traumatic brain injury.

In accordance with a further embodiment, a computer program product for monitoring a user of a helmet for a traumatic brain injury includes a non-transitory storage medium readable by a processing circuit and storing instructions for execution by the processing circuit for performing a method. The method includes monitoring a gait of the user with one or more accelerometers embedded in the uniform and analyzing, by a processor, one or more characteristics of the gait of the user. The method also includes determining whether the one or more characteristics of the gait indicate that the user may have suffered the traumatic brain injury and creating an alert that the user of the helmet may have suffered the traumatic brain injury.

BRIEF DESCRIPTION OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

DETAILED DESCRIPTION

In accordance with exemplary embodiments of the disclosure, methods, systems and computer program products for using sensors in a helmet, or another suitable piece of a uniform, to monitor a wearer for indications of a brain injury are provided. In exemplary embodiments, the sensors may include one or more of accelerometers, gyroscopes, cameras, microphones, or the like. In general, the outputs of the sensors are used to monitor one or more physical characteristics or actions of the user for signs of a traumatic brain injury, such as a concussion. In exemplary embodiments, a combination of senor readings may be used to detect a possible traumatic brain injury. In exemplary embodiments, once a possible traumatic brain injury is detected, a signal indicative of the detected traumatic brain injury may be created and transmitted.

Figure 1:
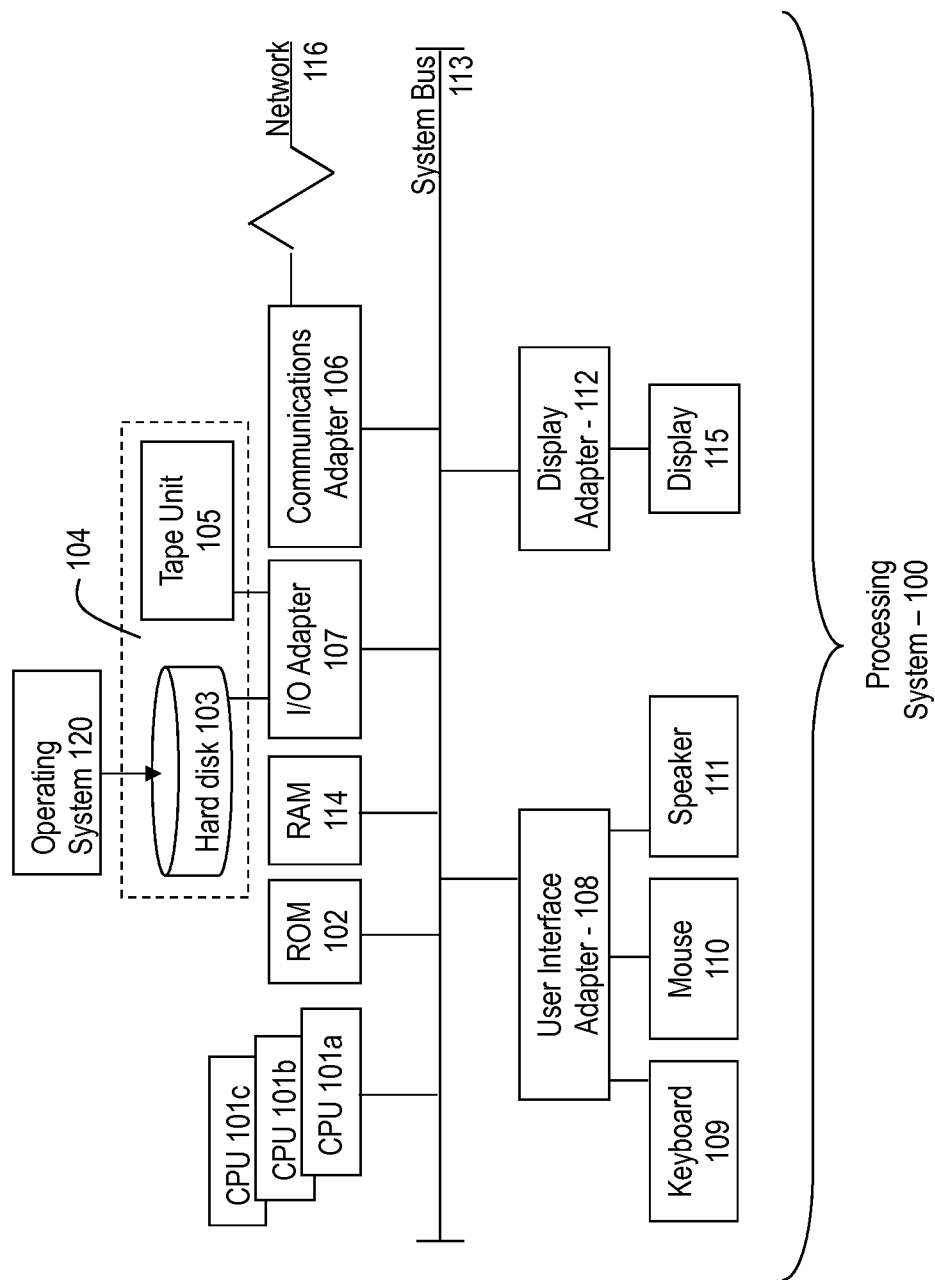
FIG. 1 is a block diagram illustrating one example of a processing system for practice of the teachings herein.

Referring to FIG. 1, there is shown an embodiment of a processing system 100 for implementing the teachings herein. In this embodiment, the system 100 has one or more central processing units (processors) 101a, 101b, 101c, etc. (collectively or generically referred to as processor(s) 101). In one embodiment, each processor 101 may include a reduced instruction set computer (RISC) microprocessor. Processors 101 are coupled to system memory 114 and various other components via a system bus 113. Read only memory (ROM) 102 is coupled to the system bus 113 and may include a basic input/output system (BIOS), which controls certain basic functions of system 100.

FIG. 1 further depicts an input/output (I/O) adapter 107 and a network adapter 106 coupled to the system bus 113. I/O adapter 107 may be a small computer system interface (SCSI) adapter that communicates with a hard disk 103 and/or tape storage drive 105 or any other similar component. I/O adapter 107, hard disk 103, and tape storage device 105 are collectively referred to herein as mass storage 104. Operating system 120 for execution on the processing system 100 may be stored in mass storage 104. A network adapter 106 interconnects bus 113 with an outside network 116 enabling data processing system 100 to communicate with other such systems. A screen (e.g., a display monitor) 115 is connected to system bus 113 by display adaptor 112, which may include a graphics adapter to improve the performance of graphics intensive applications and a video controller. In one embodiment, adapters 107, 106, and 112 may be connected to one or more I/O busses that are connected to system bus 113 via an intermediate bus bridge (not shown). Suitable I/O buses for connecting peripheral devices such as hard disk controllers, network adapters, and graphics adapters typically include common protocols, such as the Peripheral Component Interconnect (PCI). Additional input/output devices are shown as connected to system bus 113 via user interface adapter 108 and display adapter 112. A keyboard 109, mouse 110, and speaker 111 all interconnected to bus 113 via user interface adapter 108, which may include, for example, a Super I/O chip integrating multiple device adapters into a single integrated circuit.

Thus, as configured in FIG. 1, the system 100 includes processing capability in the form of processors 101, storage capability including system memory 114 and mass storage 104, input means such as keyboard 109 and mouse 110, and output capability including speaker 111 and display 115. In one embodiment, a portion of system memory 114 and mass storage 104 collectively store an operating system such as the AIX® operating system from IBM Corporation to coordinate the functions of the various components shown in FIG. 1.

Figure 2:
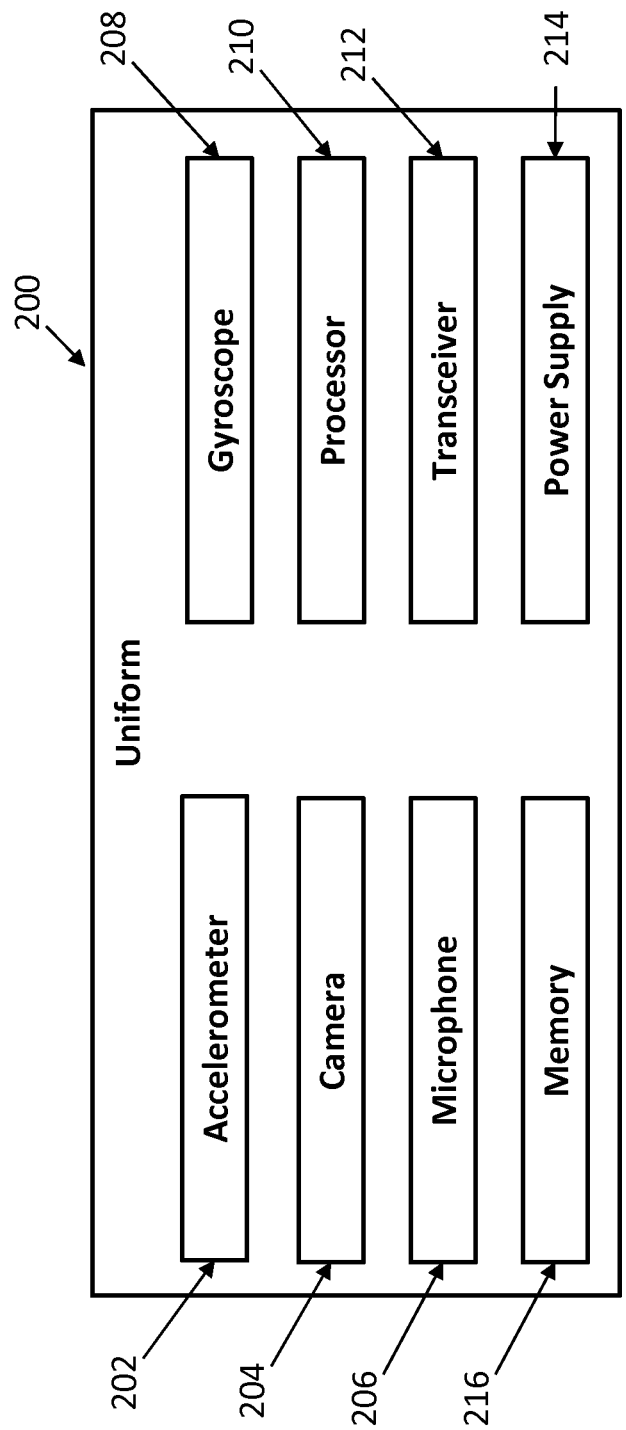
FIG. 2 is a block diagram illustrating one example of a uniform in accordance with an exemplary embodiment.

Referring to FIG. 2, a block diagram illustrating one example of a uniform 200 in accordance with an exemplary embodiment is shown. As used herein a uniform is an outfit worn by individual while participating in an activity. The term uniform may include, but is not intended to be limited to, a helmet. In exemplary embodiments, the uniform 200 includes one or more of the following an accelerometer 202, a camera 204, a microphone 206, a gyroscope 208, a processor 210, a transceiver 212, a power supply 214 and a memory 216. In exemplary embodiments, the power supply 214 may be a battery configured to provide power to one or more of the accelerometer 202, the camera 204, the microphone 206, the gyroscope 208, the processor 210 and the transceiver 212.

The processor 210 is configured to receive an output from one or more of the accelerometer 202, the camera 204, the microphone 206 and the gyroscope 208 and to determine if a user of the uniform may have suffered a traumatic brain injury based on the inputs received. In exemplary embodiments, the processor 210 may also be used to create a baseline profile of the user based on input form the accelerometer 202, the camera 204, the microphone 206 and the gyroscope 208 during a first time period and may store the baseline profile in the memory 216. The processor 210 may compare the readings from the accelerometer 202, the camera 204, the microphone 206 and the gyroscope 208 during a second time period with the stored baseline profile to make determination that the user of the uniform may have suffered a traumatic brain injury. Upon making a determination that the user of the uniform may have suffered a traumatic brain injury the processor 210 utilizes the transceiver to transmit an alert that the user of the uniform may have suffered a traumatic brain injury.

In exemplary embodiments, the processor 210 may be configured to selectively activate one of the camera 204, the microphone 206 and the gyroscope 208 based on the output received from the accelerometer 202 exceeding a threshold level. As will be appreciated by those of ordinary skill in the art, the number and placement of the various sensors (accelerometer 202, camera 204, microphone 206, and gyroscope 208) will depend upon the type of the uniform and the metrics of the user to be monitored. In exemplary embodiments, the user metrics that can be monitored include, but are not limited to, the gait of the user, the speech of the user and the eyes of the user.

Figure 3:
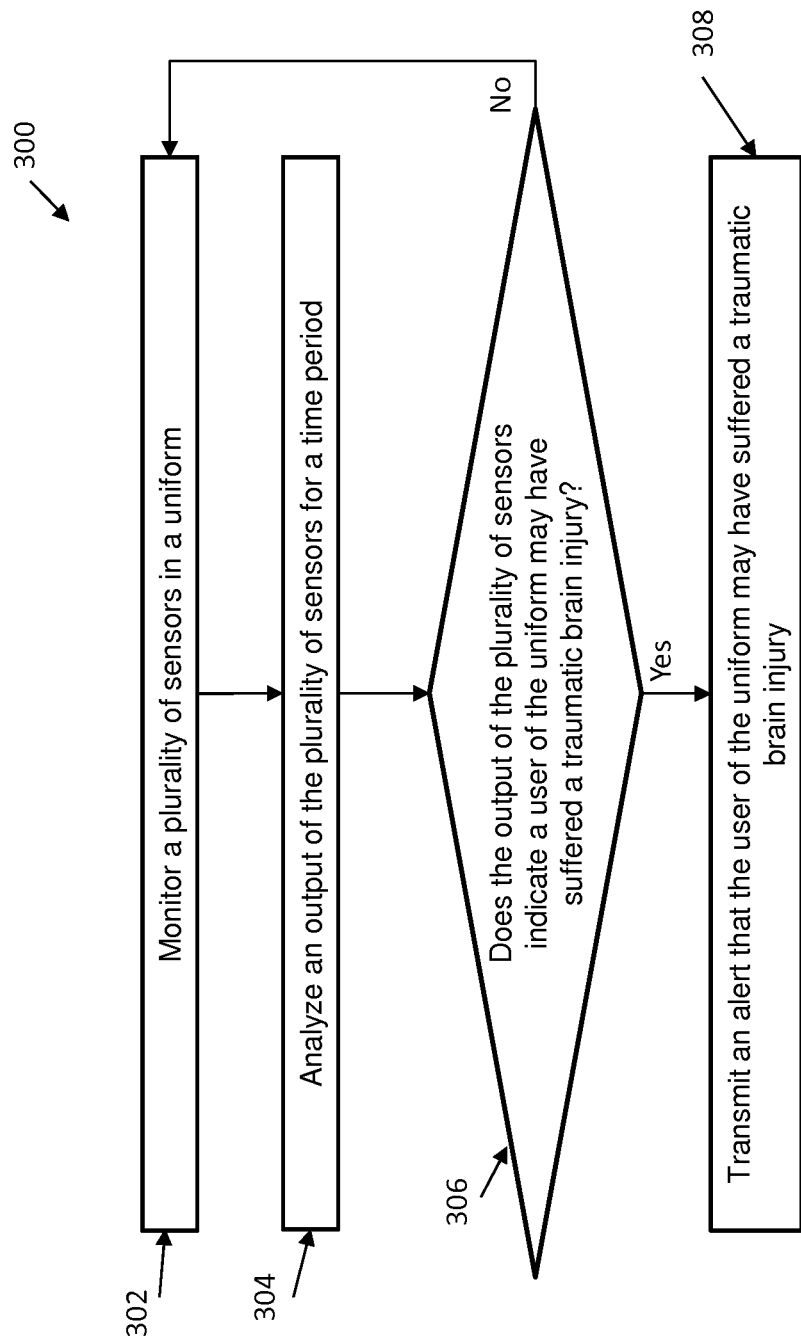
FIG. 3 is a flow diagram of a method for monitoring a user for a traumatic brain injury in accordance with an exemplary embodiment.

Referring now to FIG. 3, a flow diagram of a method 300 for monitoring a user for a traumatic brain injury in accordance with an exemplary embodiment is shown. As shown at block 302, the method 300 includes monitoring a plurality of sensors in a uniform. In exemplary embodiments, the plurality of sensors includes an accelerometer and at least one of a camera, a gyroscope and a microphone. Next, as shown at block 304, the method 300 includes analyzing an output of the plurality of sensors for a time period. In exemplary embodiments, analyzing the output of the plurality of sensors may include comparing the output of the plurality of sensors to one or more stored profiles corresponding to normal measurements from each of the plurality of sensors or to one or more thresholds for each of the plurality of sensors. As shown at decision block 306, the method 300 includes determining if the output of the plurality of sensors indicates a user of the uniform may have suffered a traumatic brain injury. If the output of the plurality of sensors indicates that the user of the uniform may have suffered a traumatic brain injury, the method 300 proceeds to block 308 and includes transmitting an alert that the user of the uniform may have suffered a traumatic brain injury. Otherwise, the method 300 returns to block 302 and continues to monitor the output of the plurality of sensors.

Figure 4:
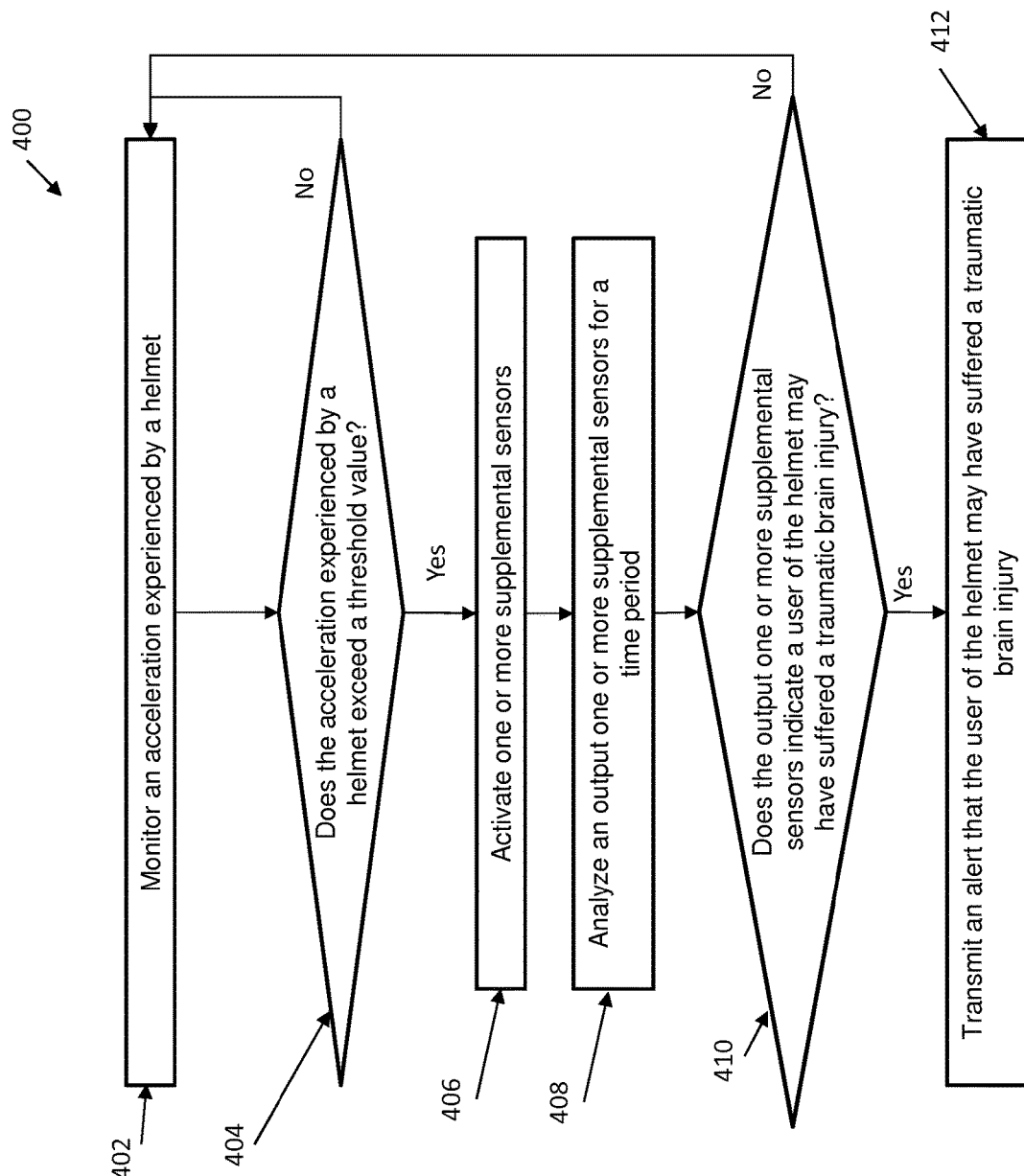
FIG. 4 is a flow diagram of another method for monitoring a user for a traumatic brain injury in accordance with an exemplary embodiment.

Referring now to FIG. 4, a flow diagram of another method 400 for monitoring a user for a traumatic brain injury in accordance with an exemplary embodiment is shown. As shown at block 402, the method 400 includes monitoring an acceleration experienced by a helmet. For example, the acceleration experienced by a helmet may be measured by one or more accelerators embedded within the helmet. Next, as shown at decision block 404, the method 400 includes determining if the acceleration experienced by the helmet exceeds a threshold value. If the acceleration experienced by the helmet does not exceed the threshold value, the method returns to block 402 and continues monitoring the acceleration experienced by the helmet. Otherwise, the method 400 proceeds to block 406 and includes activating one or more supplemental sensors. In exemplary embodiments, the one or more supplemental sensors may include a camera, a gyroscope and/or a microphone.

The method 400 also includes analyzing an output one or more supplemental sensors for a time period. In exemplary embodiments, analyzing the output of the supplemental sensors may include comparing the output of the supplemental sensors to one or more stored profiles corresponding to normal measurements from each of the supplemental sensors or to one or more thresholds for each of the supplemental sensors. As shown at decision block 410, the method 400 includes determining if the outputs of one of the one or more supplemental sensors indicate a user of the helmet may have suffered a traumatic brain injury. If the output of one of the supplemental sensors indicates that the user of the helmet may have suffered a traumatic brain injury, the method 400 proceeds to block 412 and includes transmitting an alert that the user of the uniform may have suffered a traumatic brain injury. Otherwise, the method 400 returns to block 402 and continues to monitor the acceleration experienced by the helmet.

It has been shown that the dilation of the pupil of an individual's eyes correlates with a cognitive category of the user and that pupil dilation can be indicative of a traumatic brain injury. Bleeding inside the skull caused by head injury can cause Anisocoria, which is an unequal pupil size. Accordingly, in exemplary embodiments, a helmet is provided that includes one or more cameras that are used to monitor the eyes of the wearer of the helmet for signs of a traumatic brain injury. For example, the camera may capture images of the eyes and the processor may analyze the pupil dilation of the helmet wearer. In some embodiments, the cameras may include a light source that is configured to project a light onto the eyes of the wearer of the helmet to aid in the evaluation of the pupil dilation response.

In exemplary embodiments, the processor may also utilize one or more environmental influences, such as an ambient lighting level, in determining a cognitive state and a risk category for traumatic brain injury. A plurality of cognitive states and risk categories can be created by monitoring the wearer of the helmet over time and during different states, i.e., active, inactive, playing, resting, etc. These cognitive states and risk categories can be stored and compared with real-time data collected by camera to map the user's current state to a known cognitive state and risk category. Deviations from expected results during known states can be used detect when the risk of traumatic brain injury is increased.

Figure 5:
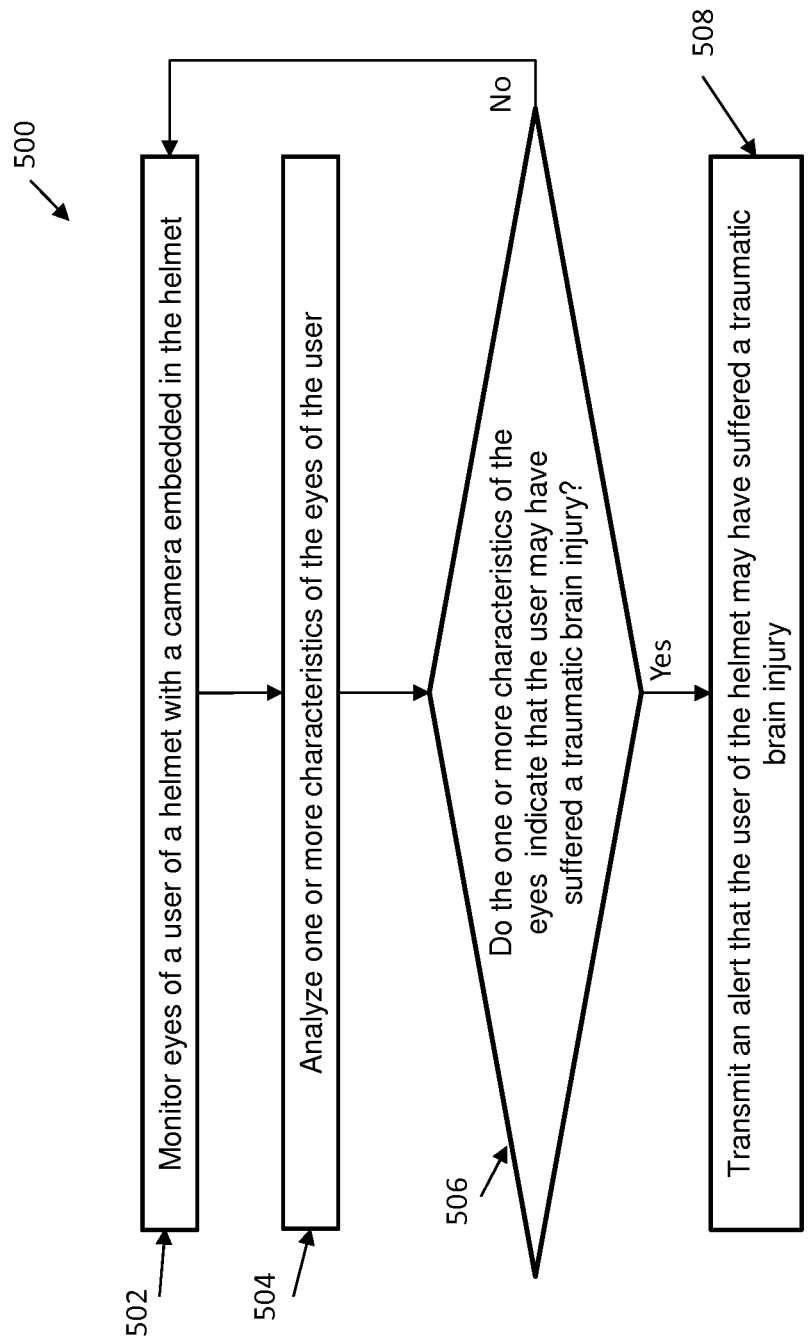
FIG. 5 is a flow diagram of a method for monitoring a user for a traumatic brain injury with a camera embedded in a helmet in accordance with an exemplary embodiment.

Referring now to FIG. 5, a flow diagram of a method 500 for monitoring a user for a traumatic brain injury with a camera embedded in a helmet in accordance with an exemplary embodiment is shown. As shown at block 502, the method 500 includes monitoring eyes of a user of the helmet with the camera embedded in the helmet. Next, as shown at block 504, the method 500 includes analyzing one or more characteristics of the eyes of the user. In exemplary embodiments, the one or more characteristics of the eyes of the user may include, but are not limited to, the pupil size of the eyes and any differences in the size of one pupil verses the other.

Next, as shown at decision block 506, the method 500 includes determining if the one or more characteristics of the eyes indicate that the user may have suffered a traumatic brain injury. If the one or more characteristics of the eyes indicate that the user may have suffered a traumatic brain injury, the method 500 proceeds to block 508 and transmits an alert that the user of the helmet may have suffered a traumatic brain injury. Otherwise, the method returns to block 502 and continues to monitor the eyes of the user of the helmet.

In exemplary embodiments, the helmet may be configured to transmit images captured by the camera to a separate system for processing and further analysis. Such transmission may be periodic, it may be triggered by a threshold image analysis by the processor embedded in the helmet, or it may be triggered by a reading from one or more sensors in the helmet, such as the accelerometer. In exemplary embodiments, the user's history of collision or medical concerns may also be used to determine a risk assessment, either by the embedded processor or the separate processing system. In addition, the helmet may be configured to provide a real-time feed of the user's cognitive state to increase the confidence level of the need for a particular alert or indication. In exemplary embodiments, an aggregate indication may be used to summarize an overall state of a group of players. This may also help to potentially identify area of risk in the dynamics of player-player interaction, overly aggressive players, playing field conditions, etc.

As mentioned, changes in pupil dilation can indicate a severe traumatic brain injury, including internal brain bleeding. Analyzing the characteristics of the eyes of the user can also include analytics of pupil dilation that subtle, and may include changes in pupil diameter and asymmetries in pupil dilation that are imperceptible to a human observer. These may then be useful in detecting milder traumatic brain injury such as concussion, which is typically invisible in medical imaging scans, and is measured instead a cognitive change. Furthermore, the use of the camera for pupil tracking can provide measures of patterns saccadic eye movements, including microsaccades, for the purpose of detecting a traumatic brain injury.

It has been shown that an analysis of an individual's speech is sufficient to assign the individual to a particular cognitive, psychological, or psychiatric category. Accordingly, in exemplary embodiments, a helmet is provided that includes one or more microphones and a processor that are used to monitor the speech of a user of the helmet for signs of a traumatic brain injury. For example, the microphones are used to capture the speech of the user of the helmet and the processor performs analysis on the collected speech. In one embodiment, the analysis can include a graphical analysis of words spoken by the user to determine cognitive state, such as by means of a speech graph. In another embodiment, the analysis can include an analysis of the prosody of the user's speech to determine the user's cognitive state and changes thereto. In many cases, a lack of prosody in the user's speech may be indicative that the user has suffered a concussion. In other embodiments, the analysis may include the detection of specific changes in the individual's speech patterns such as syllable durations and reduced peak velocity/amplitude ratios.

In exemplary embodiments, a plurality of cognitive states and risk categories can be created by monitoring the speech of the wearer of the helmet over time and during different states, i.e., active, inactive, playing, resting, etc. These cognitive states and risk categories can be stored and compared with the real-time speech data collected by microphone to map the user's current state to a known cognitive state and risk category. As a result, deviations of the current state from one of the known states can be used detect when the risk of traumatic brain injury is increased.

In exemplary embodiments, the helmet may also include a vibration detection sensor that is disposed close to skull of the wearer that can be used by the processor to disambiguate speech generated by the wearer of the helmet from the speech of other nearby individuals. In exemplary embodiments, the processor embedded in the helmet may be configured to perform a speech to text conversion. In other embodiments, the sound captured by the microphones may be transmitted to a separate system for processing and further analysis.

In exemplary embodiments, the user's history of collision or medical concerns may also be used in determining a risk assessment, either by the embedded processor or the separate processing system. In addition, the helmet may be configured to provide a real-time feed of the speech or the user's cognitive state to increase the confidence level of the need for a particular alert or indication. In exemplary embodiments, an aggregate indication may be used to summarize an overall state of a group of players. This may also help to potentially identify area of risk in the dynamics of player-player interaction, overly aggressive players, playing field conditions, etc.

Figure 6:
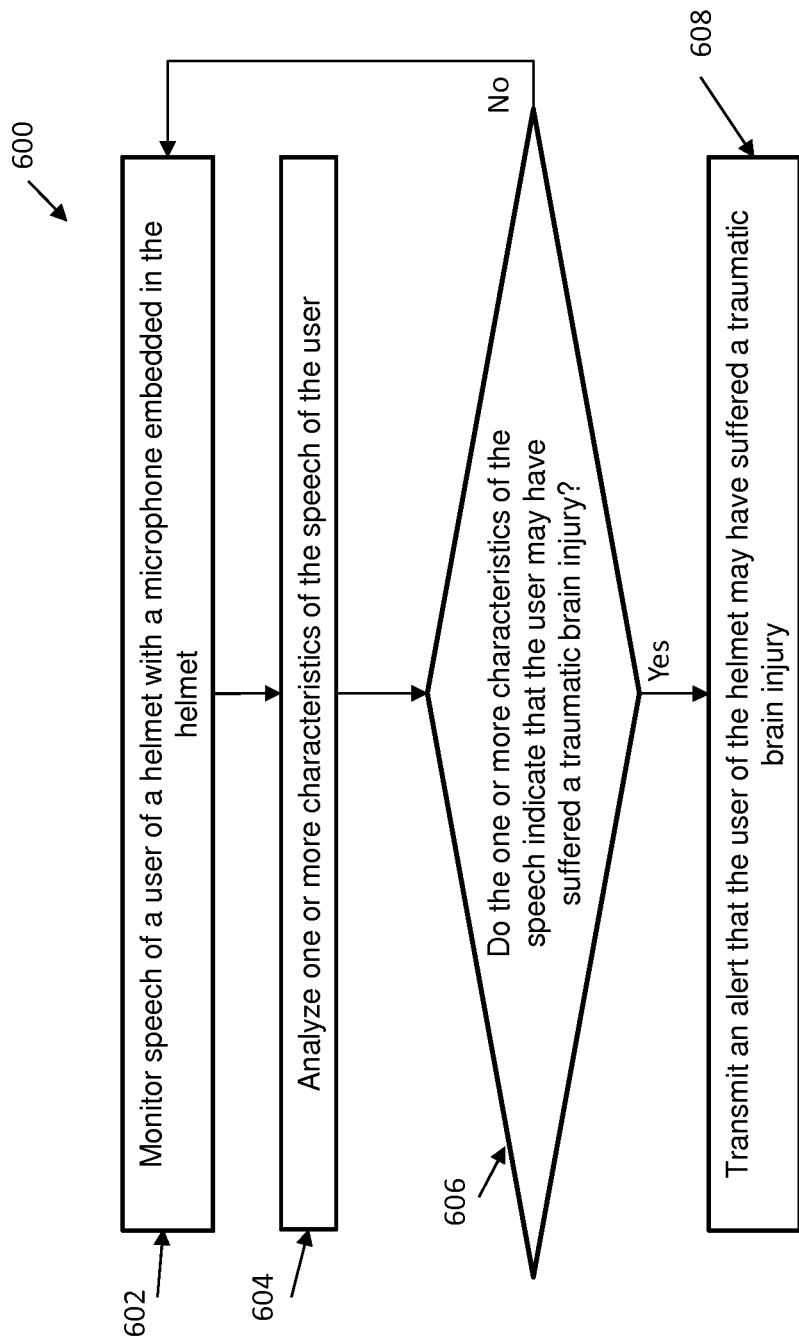
FIG. 6 is a flow diagram of another method for monitoring a user for a traumatic brain injury with a microphone embedded in a helmet in accordance with an exemplary embodiment.

Referring now to FIG. 6, a flow diagram of a method 600 for monitoring a user for a traumatic brain injury with a microphone embedded in a helmet in accordance with an exemplary embodiment is shown. As shown at block 602, the method 600 includes monitoring the speech of a user of the helmet with the microphone embedded in the helmet. Next, as shown at block 604, the method 600 includes analyzing one or more characteristics of the speech of the user. In exemplary embodiments, the one or more characteristics of the speech of the user may include, but are not limited to, words spoken by the user (via a speech graph), the prosody of the users speech, or the rate of the users speech (words/min). Next, as shown at decision block 606, the method 600 includes determining if the one or more characteristics of the speech of the user indicate that the user may have suffered a traumatic brain injury. If the one or more characteristics of the speech of the user indicate that the user may have suffered a traumatic brain injury, the method 600 proceeds to block 608 and transmits an alert that the user of the helmet may have suffered a traumatic brain injury. Otherwise, the method 600 returns to block 602 and continues to monitor the speech of the user of the helmet.

For speech traits and other cognitively correlated traits described herein, comparing a current cognitive trait to those measured previously may occur either within an individual, or across individuals. For example, the category of speech features that present after concussion may be common across individuals, even if speech features vary across individuals before concussion. In this way, detection may be simplified and not require historical data from the individual, but instead only a set of predetermined features of a concussed cohort of individuals.

It has been shown that an analysis of an individual's gait is sufficient to assign the individual to a particular cognitive category. In addition, quantitative gait analysis can be used to identify walking abnormalities, which can be used as an indicator that an individual may have suffered a traumatic brain injury. Accordingly, in exemplary embodiments, a uniform is provided that includes one or more sensors that are used to monitor the gait of a user for signs of a traumatic brain injury. For example, the uniform may include multiple accelerometers disposed in different locations of the uniform and a processor to analyze the data collected by the accelerometers. In one embodiment, the uniform may include accelerometers disposed on parts of the body to measures posture and stride and accelerometers disposed in a helmet to monitor gait. In exemplary embodiments, the system creates and stores a baseline profile of the user based on input form the accelerometers and compares the real-time readings from the accelerometers to make determination that the user of the uniform may have suffered a traumatic brain injury.

Figure 7:
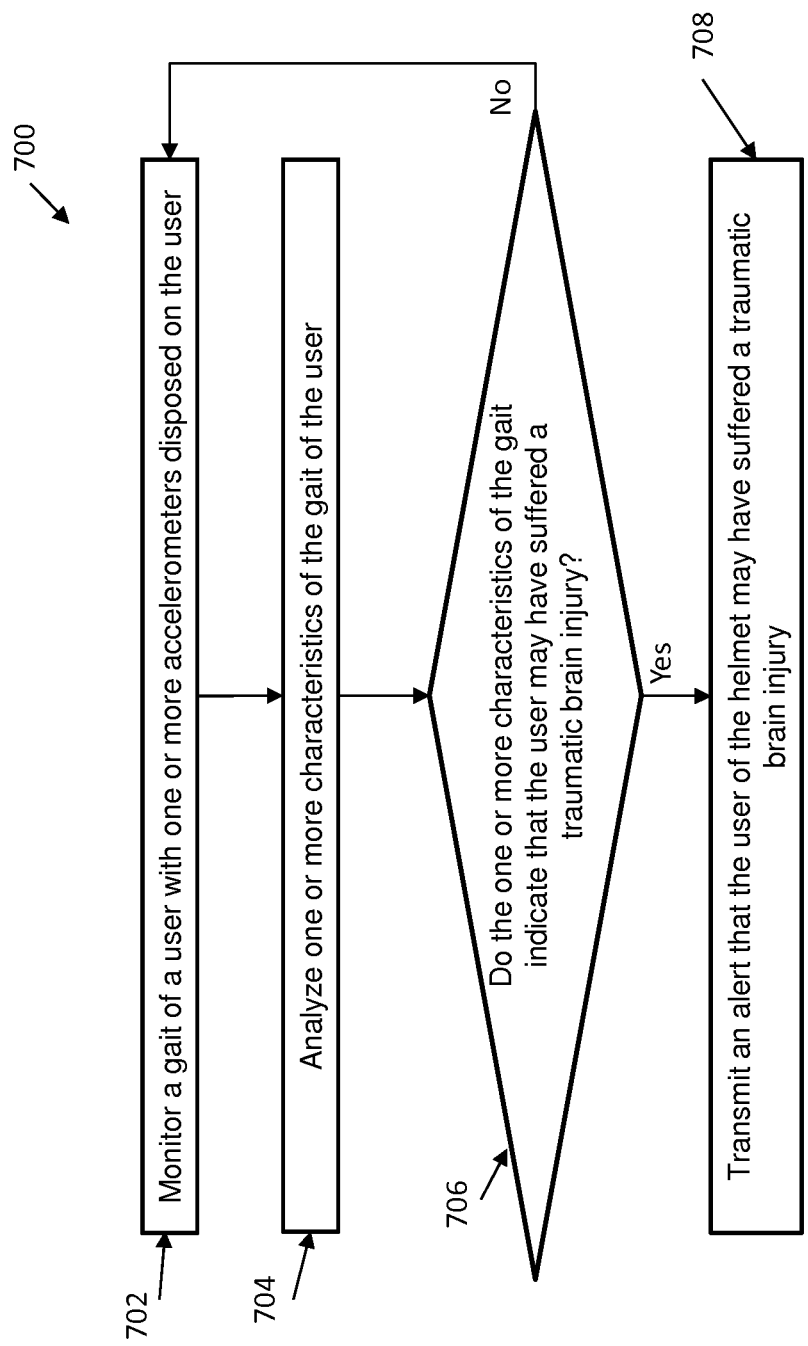
FIG. 7 is a flow diagram of a method for monitoring a user for a traumatic brain injury based on a gait of the user in accordance with an exemplary embodiment.

Referring now to FIG. 7, a flow diagram of a method 700 for monitoring a user for a traumatic brain injury based on a gait of the user in accordance with an exemplary embodiment is shown. As shown at block 702, the method 700 includes monitoring a gait of a user with one or more accelerometers disposed on the user. Next, as shown at block 704, the method 700 includes analyzing one or more characteristics of the gait of the user. In exemplary embodiments, the one or more characteristics of the gait of the user may include, but are not limited to, a duty factor and a forelimb-hindlimb (arm-leg) phase relationship. The duty factor is the percent of a total cycle which a given foot is on the ground and a forelimb-hindlimb phase is the temporal relationship between the limb pairs. Next, as shown at decision block 706, the method 600 includes determining if the one or more characteristics of the gait of the user indicate that the user may have suffered a traumatic brain injury. If the one or more characteristics of the gait of the user indicate that the user may have suffered a traumatic brain injury, the method 700 proceeds to block 708 and transmits an alert that the user of the helmet may have suffered a traumatic brain injury. Otherwise, the method 700 returns to block 702 and continues to monitor the gait of the user of the helmet.

In one embodiment, a system is provided that analyzes acceleration data received from one or more accelerometer in a uniform to determine the postural and movement indicators of a user. In exemplary embodiments, the postural and movement indicators are correlated to one of a group of play categories. In general, muscle memory would dictate that an individual would only experience slight deviations of acceleration during certain categories of play. Accordingly, the system can determine the state of play and then compare the expected acceleration data for that state of play to the observed readings. A brain or somatic injury, for example to the cerebellum, may indicated by when measures fall outside this expected range given a play category. In exemplary embodiments, the categories, or states of play, can be shared with a separate analytics processor to determine risk of certain brain injuries, given the category of play.

Figure 8:
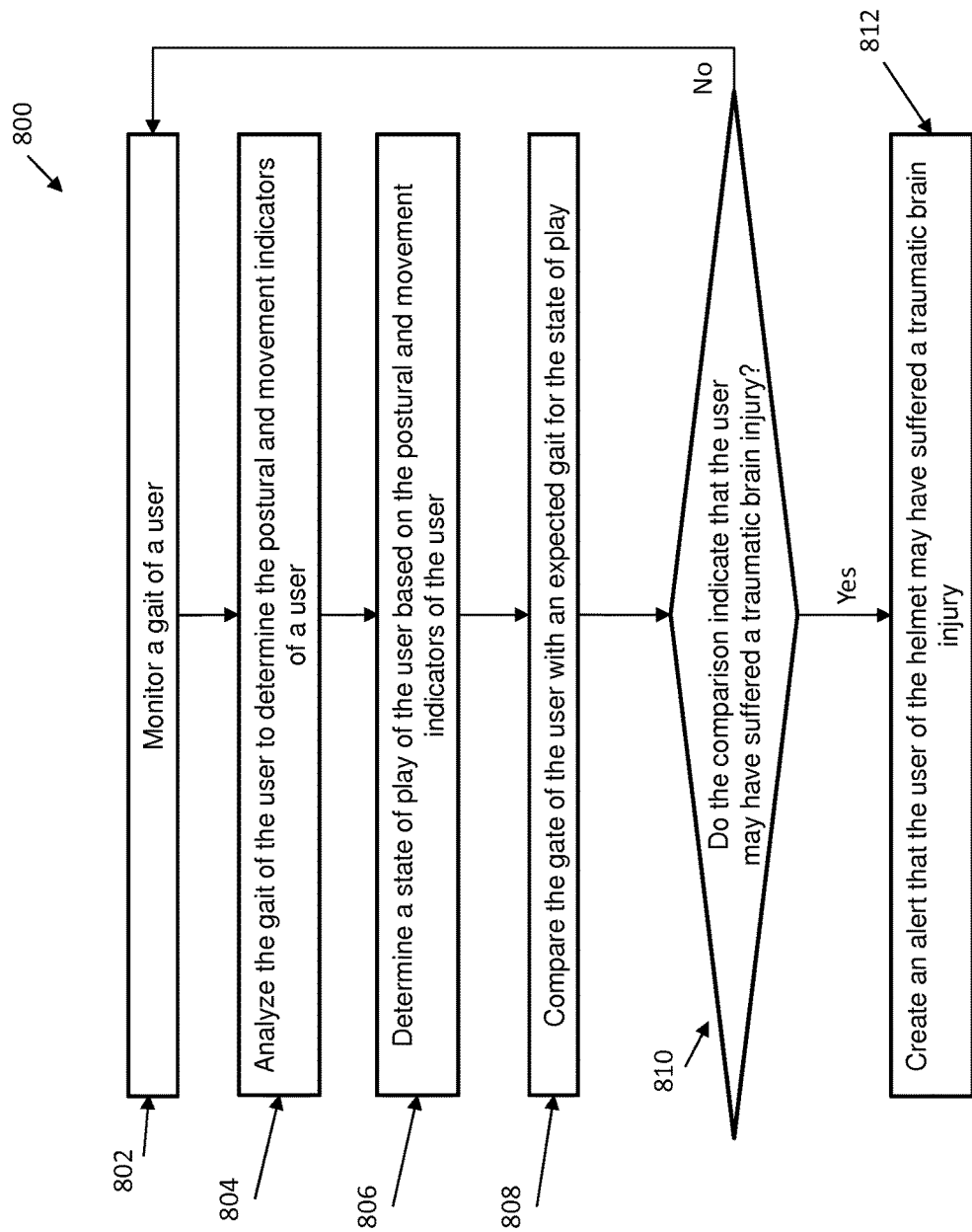
FIG. 8 is a flow diagram of another method for monitoring a user for a traumatic brain injury based on a gait of the user in accordance with an exemplary embodiment.

Referring now to FIG. 8, a flow diagram of a method 800 for monitoring a user for a traumatic brain injury based on a gait of the user in accordance with an exemplary embodiment is shown. As shown at block 802, the method 800 includes monitoring a gait of a user. In exemplary embodiments, the gait may be monitored by one or more accelerometers disposed on the user and/or by video system that monitors the movement of the user. Next, as shown at block 804, the method 800 includes analyzing the gait of the user to determine the postural and movement indicators of a user. The method 800 also includes determining a state of play of the user based on the postural and movement indicators of the user, as shown at block 806. Next, as shown at block 808, the method 800 includes comparing the gait of the user with an expected gait for the state of play. Next, at decision block 810, the method 800 includes determining if the comparison indicates that the user may have suffered a traumatic brain injury. If the comparison indicates that the user may have suffered a traumatic brain injury, the method 800 proceeds to block 812 and creates an alert that the user of the helmet may have suffered a traumatic brain injury. Otherwise, the method 800 returns to block 802 and continues to monitor the gait of the user.

Figure 9:
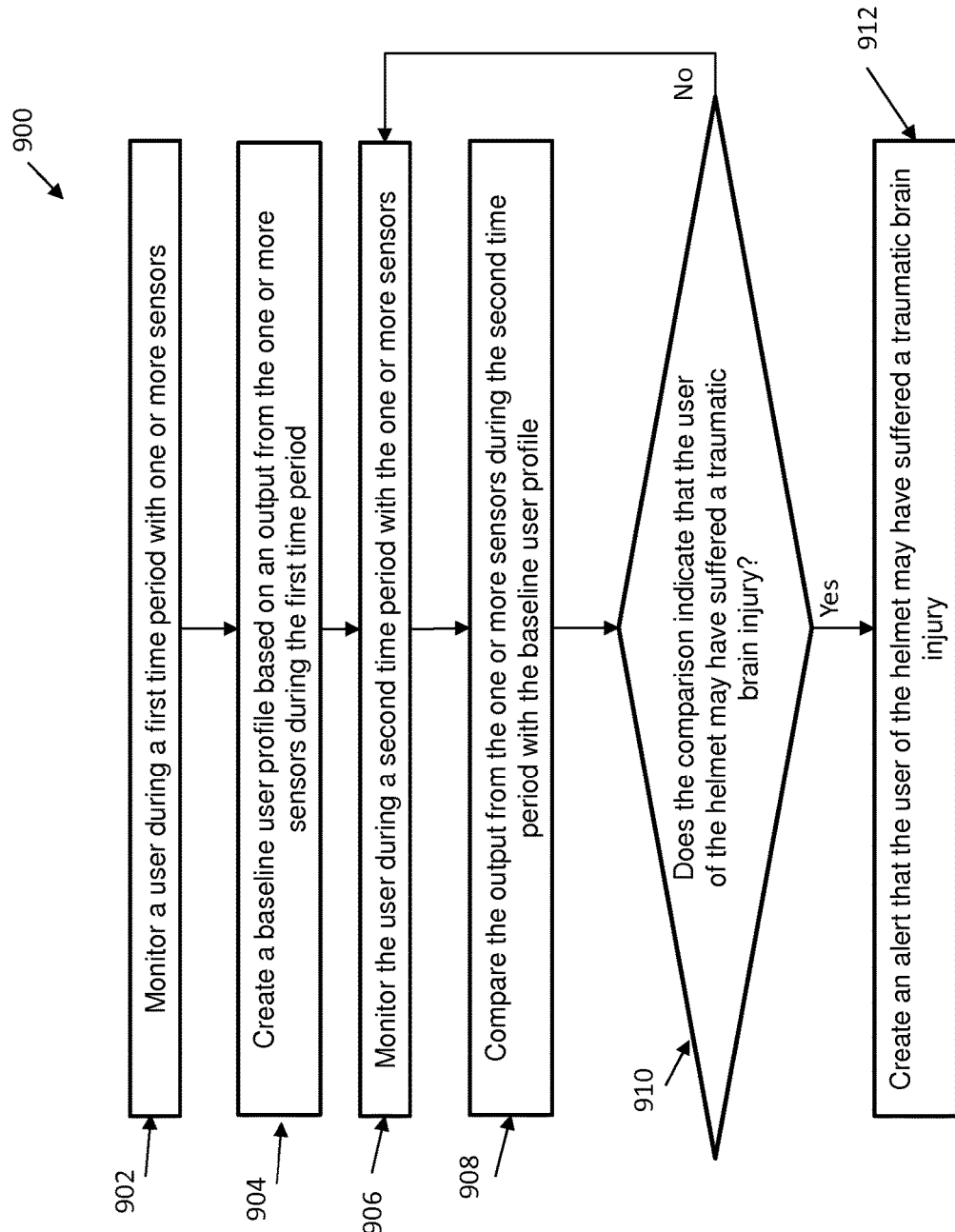
FIG. 9 is a flow diagram of a further method for monitoring a user for a traumatic brain injury in accordance with an exemplary embodiment.

Referring now to FIG. 9, a flow diagram of a method 900 for monitoring a user for a traumatic brain injury in accordance with an exemplary embodiment is shown. As shown at block 902, the method 900 includes monitoring a user during a first time period with one or more sensors. Next, as shown at block 904, the method 900 includes creating a baseline user profile based on an output from the one or more sensors during the first time period. The method 900 also includes monitoring the user during a second time period with the one or more sensors, as shown at block 906. Next, as shown at block 908, the method 900 includes comparing the output from the one or more sensors during the second time period with the baseline user profile. Next, as shown at decision block 910, the method 900 includes determining if the comparison indicates that the user may have suffered a traumatic brain injury. If the comparison indicates that the user may have suffered a traumatic brain injury, the method 900 proceeds to block 812 and creates an alert that the user of the helmet may have suffered a traumatic brain injury. Otherwise, the method 900 returns to block 906 and continues to monitor the user.

Technical effects and benefits include uniforms that are configured to monitor individuals for signs of a traumatic brain injury based on a variety of factors. In addition, the uniforms can be configured to provide an indication that a user has suffered a traumatic brain injury with an increased confidence by monitoring multiple different characteristics of the user. Such uniforms and helmet can be utilized by soldiers, athletes, and other individuals at risk for traumatic brain injuries.

Analysis of measurements across sensors may make use of Bayes' rule. The confidence determining step 910 determines a confidence level indicating a likelihood of a user to have a traumatic brain injury. For example, a confidence determining module may determine that a user has had a concussion. In some embodiments, the confidence determining module uses Bayesian inference to compute the conditional probability P(concussion|evidence), where evidence includes any measure of the user. P(concussion|evidence) indicates the probability of concussion given that evidence is true, meaning it indicates the probability or level of brain injury that the user has had, given that the user has produced certain measures. If the probability is sufficiently high (i.e., above a threshold probability), the confidence determining module determines that it is very likely the user has had a concussion.

The conditional probability P(concussion|evidence), which is the probability of concussion given that evidence is true, may be computed using the equation (1) according to Bayes rule:

$$P(\text{concussion} | \text{evidence}) = \frac{P(\text{evidence} | \text{concussion}) \times P(\text{concussion})}{P(\text{evidence})} \quad (1)$$

where P(concussion) and P(evidence) are the probabilities of concussion and evidence, respectively, and P(evidence|concussion) is the probability of evidence given that concussion is true. In some embodiments, P(evidence|concussion) is computed using a probabilistic model that relates concussion (i.e., the condition) to evidence (i.e., the measures), and this model is learned in advance using, e.g., Naive Bayes, or Bayesian Network models. In the absence of any other evidence (i.e., using only the expressions), P(concussion) is a uniform distribution—there is a certain probability that the user has a concussion and a certain probability that the user does not have a concussion before the measurement begins. P(concussion), however, may not be a uniform distribution if evidence other than the expressions of the user is considered before the conversation begins. For instance, P(concussion) may start from a 30% probability that the user is concussed. In such cases, the number of measures needed for P(concussion|evidence) to exceed the threshold probability may be fewer.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A method for monitoring a user of a uniform for a traumatic brain injury, the method comprising:
   monitoring an acceleration of a head of a user with a plurality of sensors embedded in the uniform, wherein the uniform comprises a helmet and an outfit worn by the user;
   wherein the plurality of sensors comprise a gyroscope and an accelerometer;
   wherein the gyroscope is embedded in the helmet;
   wherein the accelerometer is embedded in the outfit;
   selectively activating the gyroscope to monitor one or more characteristics of a gait of the user based on the acceleration exceeding a threshold level;
   measuring, by the accelerometer a stride of the user;
   determining that the one or more characteristics of the gait and the measured stride of the user indicate that the user may have suffered the traumatic brain injury, wherein the one or more characteristics of the gait of the user comprises a duty factor and a forelimb-hindlimb phase relationship; and
   wherein the determination that the one or more characteristics of the gait indicate that the user may have suffered the traumatic brain injury is based on a comparison of the one or more characteristics of the gait of the user to a baseline reading of the one or more characteristics of the gait and a baseline measurement of the stride of the user;
   creating an alert that the user of the helmet may have suffered the traumatic brain injury.

2. The method of claim 1, wherein the analyzing includes determining postural and movement indicators of the user.

3. The method of claim 1, further comprising transmitting the alert to a separate computer system for processing and further analysis.

* * * * *